US008325037B2

(12) United States Patent
Luemkemann et al.

(10) Patent No.: US 8,325,037 B2
(45) Date of Patent: Dec. 4, 2012

(54) ENERGY SAVING MEDICAL DEVICE

(75) Inventors: Frank Luemkemann, Jena (DE); Heino Weigand, Jena (DE)

(73) Assignee: Carl Zeiss Meditec AG, Jena (DE)

(*) Notice: Subject to any disclaimer, the term of this patent is extended or adjusted under 35 U.S.C. 154(b) by 234 days.

(21) Appl. No.: 12/675,819

(22) PCT Filed: Aug. 30, 2008

(86) PCT No.: PCT/EP2008/007125
§ 371 (c)(1),
(2), (4) Date: Apr. 9, 2010

(87) PCT Pub. No.: WO2009/030446
PCT Pub. Date: Mar. 12, 2009

(65) Prior Publication Data
US 2010/0308994 A1    Dec. 9, 2010

(30) Foreign Application Priority Data

Sep. 4, 2007   (DE) .......................... 10 2007 041 962

(51) Int. Cl.
*G08B 21/00* (2006.01)
(52) U.S. Cl. ...................... 340/540; 340/573.1; 340/7.27
(58) Field of Classification Search .................. 340/540, 340/7.27, 573.1, 546, 553, 555, 556, 557, 340/562, 552, 572.1, 626, 5.2
See application file for complete search history.

(56) References Cited

U.S. PATENT DOCUMENTS

| 3,830,562 | A | | 8/1974 | McGrann et al. |
|---|---|---|---|---|
| 5,070,329 | A | * | 12/1991 | Jasinaki ........................ 340/7.27 |
| 5,387,952 | A | | 2/1995 | Byer |
| 5,790,234 | A | | 8/1998 | Matsuyama |
| 6,259,486 | B1 | * | 7/2001 | Mahvi ............................ 348/553 |
| 7,679,221 | B2 | * | 3/2010 | Kim ............................... 307/116 |
| 2003/0025604 | A1 | * | 2/2003 | Freeman .................... 340/573.1 |
| 2007/0194939 | A1 | * | 8/2007 | Alvarez et al. ............. 340/573.1 |
| 2012/0026466 | A1 | * | 2/2012 | Zhou et al. ..................... 351/214 |

FOREIGN PATENT DOCUMENTS

| DE | 10 2004 031 087 | 1/2006 |
|---|---|---|
| DE | 101 64 758 | 12/2006 |
| WO | WO 2005/020417 | 3/2005 |

OTHER PUBLICATIONS

Patent Abstracts of Japan; Publication No. 2001187021; Publication Date Jul. 10, 2001.
Patent Abstracts of Japan; Publication No. 2006026000; Publication Date Feb. 2, 2006.
Patent Abstracts of Japan; Publication No. 11249064; Publication Date Sep. 17, 1999.

* cited by examiner

*Primary Examiner* — Daniel Previl
(74) *Attorney, Agent, or Firm* — Frommer Lawrence & Haug LLP

(57) ABSTRACT

The invention is directed to a medical device comprised of at least one device part that is electrically operated and can be switched between an idle state and an operating state and a method of controlling such device. A control unit is provided which switches an electrically operated device part from the operating state to the idle state. Alternatively or in addition, a person detector and a control unit are provided, wherein a control unit switches the device part to the operating state in case the person detector detects the presence of a person at a distance from the device. Alternatively or in addition, an operating control is provided for manually switching the device from the operating state to the idle state.

17 Claims, 3 Drawing Sheets

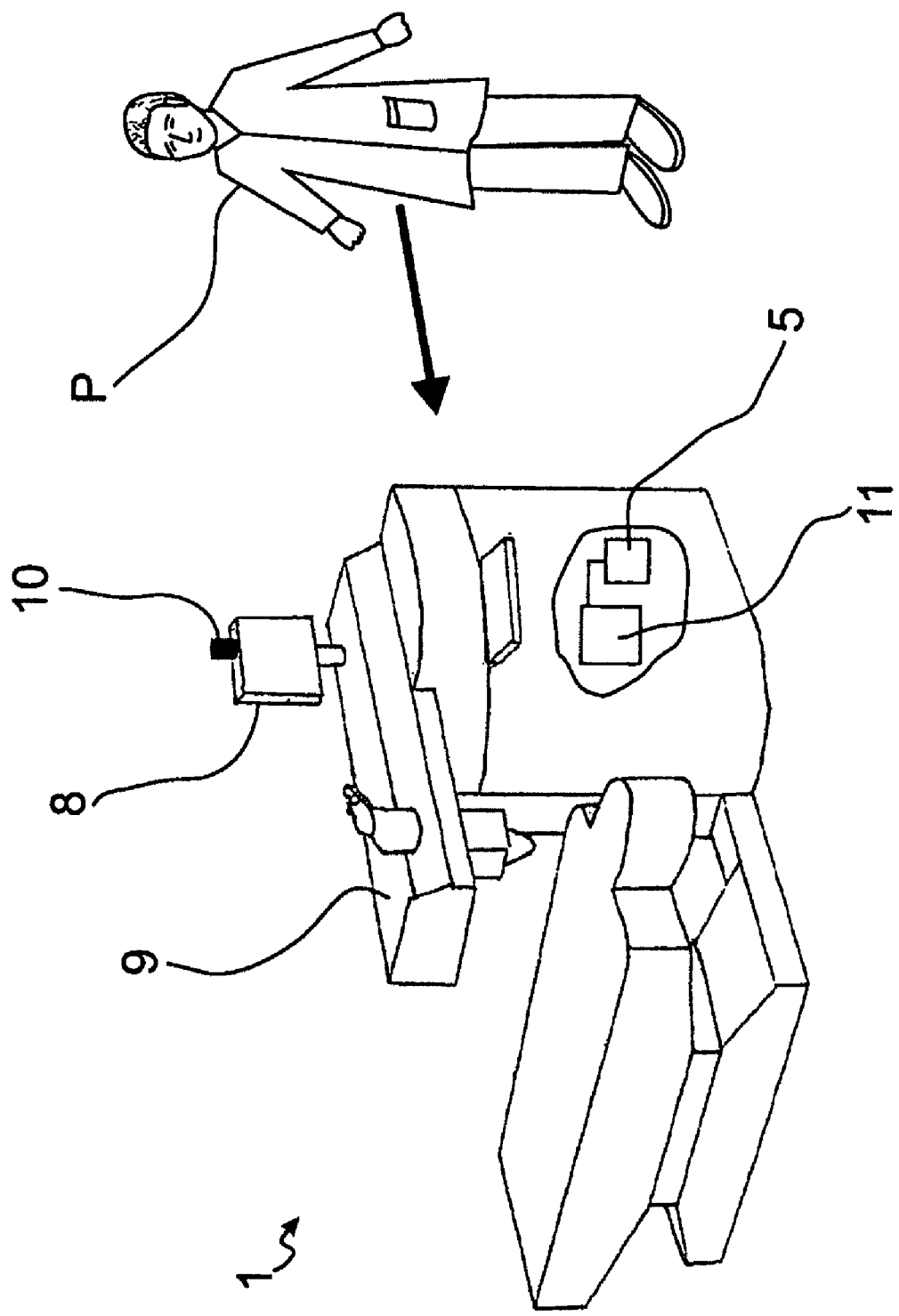

ENERGY SAVING MEDICAL DEVICE

The present application claims priority from PCT Patent Application No. PCT/EP2008/007125 filed on Aug. 30, 2008, which claims priority from German Patent Application No. 10 2007 041 962.9 filed on Sep. 4, 2007, the disclosure of which is incorporated herein by reference in its entirety.

BACKGROUND OF THE INVENTION

1. Field of the Invention

The invention is directed to a medical device in which at least one device part can be switched between an idle state and an operating state, and to a control method for a device of this kind.

2. Description of Related Art

Generally, medical devices contain electric component parts which consume energy in the operating state and, in so doing, generate waste heat. The cooling of such component parts consumes additional electric energy, usually leads to heating of the surrounding space, and generates noise of varying intensity, for example, because of rotating fans.

Medical devices in the office of an established doctor are typically switched on at the start of office hours and are switched off at the end of office hours so as to be constantly available. In hospitals, medical devices are often switched on round the clock for the same reason. In both cases, the devices, while not in continual use, may still pose significant health risks for operating personnel because of the waste heat and possible noise because they are permanently switched on in the operating state. Above all, more than one device generating heat and noise in one room creates stress which is not always consciously perceived.

On the other hand, with other medical devices, the operating state is not conspicuous aurally or visually so that it may easily be overlooked that a device is still in the operating state after being used, that is, after an examination or treatment and after the patient's visit is concluded. Since devices of this kind do not generate an immediately perceptible burden on the operating personnel, individuals may neglect to switch off the device until the next time it is used.

However, it is generally worthwhile to keep the energy requirement of technical equipment as low as possible in order to achieve low operating costs and a good ecological cost-benefit ratio. Also, medical devices are sometimes operated with storage cells or batteries either in case of a power outage or in areas without electric line voltages. In devices of this kind, it is especially important not to consume energy unnecessarily.

Further, most electric or electronic components have only a limited lifetime which is usually expressed by an average number of expected operating hours before failure (MTTF or MTBF). Therefore, when a medical device which is only used intermittently is operated full-time, the operating costs are higher than when the medical device is operated as needed. In addition, more frequent need to exchange a defective component worsens the ecological cost-benefit ratio of the device.

SUMMARY OF THE INVENTION

Therefore, it is the object of the invention to make it possible to reduce the energy consumption of medical devices.

According to the invention, this object is met by the combinations of features of the independent claims. Advantageous embodiments of the invention are indicated in the dependent claims.

According to the invention, a medical device with a switchable device part is provided with a control unit which switches at least the device part from the operating state to the idle state at the expiration of a predeterminable or predetermined period of time in which the control unit determines that the device is not in use. In the idle state, at least of the device part, the device consumes less energy and any cooling generates less noise or none at all. Thanks to the invention, the device or device part need not be switched off manually by operating personnel. The invention automatically prevents unwanted permanent operation of a medical device. Therefore, energy consumption is reduced in devices which are used only intermittently. Better use is made of the limited lifetime of critical components. In many device parts, the lifetime can even be increased by an electronic control which causes the device to enter the operating state gradually (soft start). Accordingly, the ecological cost-benefit ratio is improved in multiple respects.

In another aspect of the invention, a medical device with a switchable device part is provided with a person detector and a control unit which switches at least the device part into the operating state when the person detector detects the presence of a person at a distance from the device. A lead time or warm-up period (designated hereinafter as startup time) of a medical device from the idle state cannot be shortened without negative side effects. However, by detecting a person who is still at a distance, a necessary lead time or warming up can be initiated in advance so that the medical device is ready to operate immediately or, at most, after a slight delay by time the detected person arrives. After use, the device or device part can be restored to the idle state. Because the device is automatically made ready to operate immediately or after only a slight delay, there is no longer any reason to leave the medical device in the operating state permanently. In this way, the invention efficiently reduces the energy consumption of the medical device.

In preferred embodiments, a person who is at a greater distance from the device than that required for using the device, particularly a person at a distance of at least 1 m from the device, can be detected by the person detector. In this way, it is possible for devices having a longer startup time to be ready to operate without delay.

The control unit advantageously first determines whether the detected person approaches the device and only switches into the operating state when an approach can be determined. This prevents the operating state from being switched on unnecessarily. For example, when a door is open, the device can be switched to the operating state when a person enters, but not when persons pass by in the corridor in front of the door.

In another aspect of the invention, a touch-sensitive operating control, preferably not an operating switch, is provided as person detector and a control unit is provided, and the control unit switches at least the device part into the operating state when the person detector detects that a person touches the operating control. In this aspect, the operating personnel need not actuate a switch to make the medical device operational. In devices with a short startup time, the time from when an operating component is first touched, for example, when fitting to a patient's body size, to the start of an examination or treatment is sufficient. The device is then ready to operate without a noticeable delay. After use, the device or device part can be returned to the idle state. Because the device is automatically made ready to operate immediately or after only a slight delay, there is again no longer any reason to leave the medical device in the operating state permanently.

Accordingly, the energy consumption of the medical device is also efficiently reduced in this aspect.

This aspect of the invention can advantageously be combined with the detection of a person still at a distance in order to acquire the near range and far range of the device environment.

In a particularly preferred embodiment form of a medical device according to the invention, in addition to switching on based on detection of a person, the control unit switches at least the device part from the operating state to the idle state after the expiration of a predeterminable or predetermined time period in which the control unit determines that the device has not been used and/or in which the person detector does not detect any persons. This maximizes the reduction of energy consumption. The automatic time-based switching off prevents unintentional permanent operation of the device. The limited lifetime of critical components is more fully exploited. The ecological cost-benefit ratio is accordingly improved in multiple respects.

Depending on the construction of the person detector, a non-use period can elapse when there is a longer period of inactivity or in the absence of use in a form capable of detection. In embodiment forms with time-based switching to the idle state, the control unit advantageously emits an advance warning signal at a predeterminable or predetermined advance warning time before the time period expires. This allows the operating personnel to carry out a brief operating action detectable by the control unit without further effect or merely to move, so that the time period of non-use ends and the pending switching into the idle state can be prevented.

Preferably, a person in an architectural interior, in a room area in the surroundings of the device, or at a determined location can be detected by the person detector. By limiting the detection area, an unnecessary switching into the operating state can be prevented. The energy consumption can be minimized in this way.

In a preferred embodiment form, the person detector is constructed as a motion detector. In this respect, all sensors which can determine movements and/or temperature changes in a definite spatial area, for example, a fixed solid angle, for example, passively by means of infrared radiation or sound or actively by means of sound, ultrasound or microwaves or combinations thereof, are considered to be motion detectors. Such motion detectors, which are known per se, are available at low cost. They can advantageously monitor a large solid angle area. For example, a defined space can be detected over a plane angle of 360° around the device at low cost. Accordingly, for example, a plurality of devices in the same architectural space can monitor different parts of the room. In this way, a plurality of devices or all devices can be prevented from being switched on simultaneously as soon as a person enters the room. A plurality of monitored parts of the room can also overlap or correspond in a planned manner when a plurality of devices are needed for a certain activity in any case. Generally, a plurality of medical devices or all medical devices in one room can be connected to the same person detector.

In a preferred embodiment form, the person detector is constructed as an acceleration sensor. Every moving person generates concussions in the floor which propagate on all sides as spatial waves and as surface waves also through tables and stands. These concussions can be determined on all sides of the device in an economical manner with respect to space and cost by an acceleration sensor of appropriate sensitivity. An approaching person can be identified in an economical manner based on the increasing amplitude of the concussions. The monitored spatial area can be limited by a lower amplitude limit for detection.

In another preferred embodiment form, the person detector is constructed as an inductive, capacitive or microwave-based proximity sensor. This is also an inexpensive form of person detection.

In another preferred embodiment form, the person detector is constructed as a short-range wireless receiver, and a short-range wireless transmitter is provided for the person to be detected. In this way, individual persons can be granted authority to switch to the operating state. Short-range wireless is any form of local communications by means of radio waves, particularly within a distance range of up to 100 m, for example, RFID, Bluetooth, a wireless local area network (WLAN), the GSM standard, or so-called near field communication (NFC). In particular, short-range wireless transmitters for the person to be detected can be active or passive transponders. For example, transponders can be sewn into the uniforms of all personnel operating a device in a department of a hospital. This also ensures that uniforms are actually worn. Alternatively, existing access authorization information from access authorization devices such as RFID chip cards can be used so that no additional transponders are required. This embodiment form also minimizes energy consumption because devices cannot be switched to the operating state unnecessarily by unauthorized persons.

Access authorization devices such as RFID chip cards can also be used in general to limit access to the medical device based on their access authorization information. For example, particularly apart from switching the operating state or the idle state of a device part, the operating personnel can be granted access only to predetermined functions depending on individual access rights, for example, to maintenance functions or cleaning functions (e.g., for nonmedical personnel), device settings and patient data as well as access to measurements and diagnostic data (for example, for medical assistants) or initiating and/or performing a diagnostic measurement and/or therapeutic treatment (for example, for medical personnel). Security-related control depending on access rights is also possible. For example, the device can be set up in such a way that an ophthalmic laser can be switched on only in the presence of a person with opthalmology access rights and special laser authorization. The laser authorization can be given, for example, only to persons specially trained in the handling of lasers. As an alternative possibility, protective devices, for example, protective screens against laser radiation, can be deactivated only by persons with special access rights, i.e., for example, with opthalmology access rights and special laser authorization as in the preceding example. An unintentional switching on of the laser can be prevented by both alternatives.

To this end, the access authorization information to be determined from the access authorization device can comprise either a simple personal identification quantity or direct individual access rights. In the case of a simple personal identification quantity, the control unit interrogates the actual access rights of the detected person, advisably via an independent data link, in a central monitoring unit. The central monitoring unit should be outfitted with a corresponding database. The monitoring of access authorization by comparing the actual access rights of the detected person to the required access rights which are predetermined according to function can be carried out either in the control unit or in the remote monitoring unit. In the latter case, the control unit upon interrogation also sends the necessary access rights for the function currently required by the operating personnel to the central monitoring unit.

In another embodiment form, the person detector is constructed as a pressure contact on a seat or examination table for a person, preferably a patient. As soon as the person takes a seat, the medical device is switched to the operating state. As a rule, the patient is already on a chair or examination table in front of the operating personnel for examination and/or treatment and accordingly triggers the switching to the operating state. Therefore, the medical device is already ready to operate when the operating personnel wants to use the device on the patient.

The pressure contact is advantageously designed to store pressure energy. Accordingly, a wireless connection can be used between the pressure contact and the medical device without having to regularly change a battery in the chair or examination table or charge a storage cell.

The different embodiment forms of the person detector can be combined optionally. For example, different ranges can be detected. For example, a distance-resolving acceleration sensor can be combined with touch-sensitive operating controls so that when the patient and operating personnel are virtually motionless an automatic switching off can be prevented during an examination and/or treatment which cannot otherwise be determined.

The response of the medical device to the detection of a present person or approaching person can be designed in multiple stages. For example, different device parts can be switched to the operating state at different stages. In so doing, the device parts can be switched to their operating state alternately or cumulatively from one stage to the next. The stages can be defined depending on access authorization information, for example. Depending on the access authorization of the detected person, different device parts or device part groups are then switched to the operating state. For nonmedical personnel, for example, only a control computer, but not a treatment unit, is switched on so that maintenance work is possible. Alternatively or in addition, the stages can be defined depending on the distance of the person from the device insofar as distance-resolved detection is possible. For example, more and more device parts can be switched to the operating state by stages as the distance decreases. Distance ranges can be defined for this purpose. Preferably, those device parts with the longest startup times are switched to the operating state first, i.e., when detection occurs at the farthest distance range, and those device parts with the shortest startup time and/or the highest energy consumption and/or the greatest wear (particularly during the switch-on process) are switched to the operating state last, i.e., when detection takes place at the closest distance range.

In a particularly preferred aspect of the invention, the device is an ophthalmic device, particularly a slit lamp, a fundus camera, a device for measuring internal dimensions of the eye, or a laser, particularly in refractive surgery. Ophthalmic devices generally contain a high-power light source with corresponding energy consumption. Therefore, they derive special advantage from the reduced consumption according to the invention. With respect to lasers, temperature stabilization is a large consumer which can profit from the invention. Due to the risk of injury resulting from a laser that is accidentally active, automatic switching off and/or switching on according to the invention also increases operating safety.

In an advantageous manner, it is possible that a reduced operating voltage other than zero is applied to the device part in the idle state. Accordingly, the device or device part need not be switched off completely. In this way, the operating state can be restored more quickly in spite of the reduced energy consumption in the idle state. This idle state with reduced operating voltage can be maintained, for example, by a battery buffer.

Preferably, an operating control for manually switching the device from the operating state to the idle state is provided at the medical device in addition to or as an alternative to a time-based automatic switching into the idle state. Therefore, the operating personnel can switch the device actively into the idle state immediately after use. Accordingly, it is not necessary to wait until a time period for non-use has elapsed, which reduces energy consumption.

The control unit and/or the person detector need not necessarily be arranged in or at the medical device, but rather can be located separately or together in an external unit while functioning in the same manner. The external units can be arranged optionally given a suitable positioning of the person detector. For example, the person detector can be a light barrier arranged at the entrance to a room. A multi-channel light barrier is preferably used so that it is possible to distinguish between entering and exiting the room. Switching to the operating state is then carried out only when the room is entered and switching to the idle state, if provided, is carried out when the room is exited. A switch-on delay can be provided for this purpose so that the device part is not switched to the operating state in the event of a short interval between entering and (re-)exiting. A switch-off delay can also be provided so that the device part is not switched to the idle state in case of a short interval between exiting and (re-)entering.

The invention comprises the control processes to be carried out by the control unit, particularly in the form of a computer program.

BRIEF DESCRIPTION OF THE DRAWINGS

FIG. 3 a schematic view of an ophthalmic excimer laser with motion detector.

DETAILED DESCRIPTION OF EMBODIMENTS

Identical parts have the same reference numbers in all of the drawings.

Figure 1:
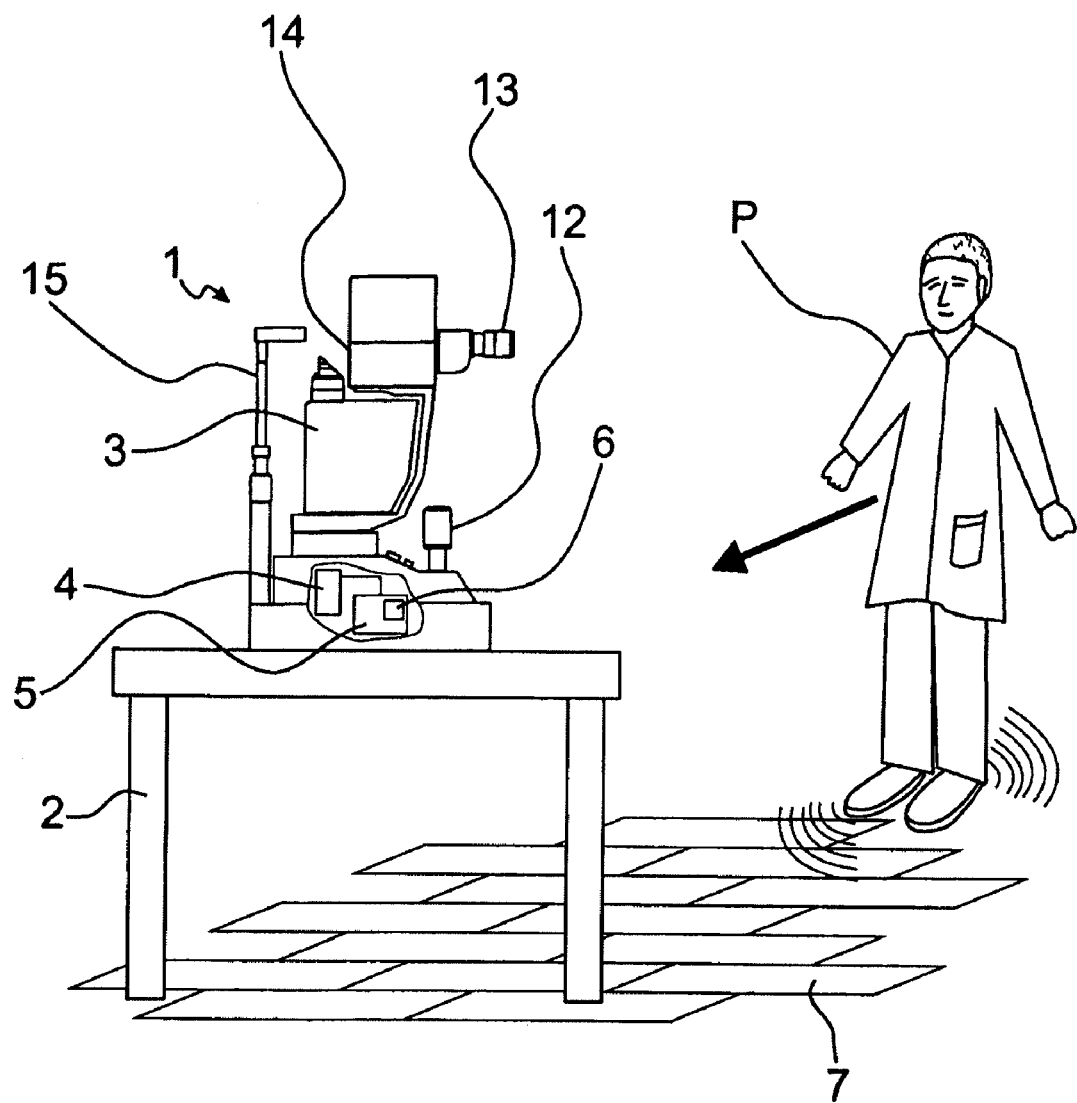
FIG. 1 a schematic view of a slit lamp with acceleration sensor and touch-sensitive operating control.

FIG. 1 schematically shows a medical device 1 in the form of a slit lamp which is arranged, for example, on a table 2. The slit lamp 1 is outfitted with an illumination unit 3, known per se, containing a halogen lamp (not shown) and a laser (not shown). The halogen lamp is supplied with electrical power by an adjustable power supply 4. The power supply 4 of the halogen lamp is connected to a control unit 5 which can regulate the electric voltage supplied to the halogen lamp by the power supply 4. An acceleration sensor 6 in the form of an integrated circuit is integrated in the control unit 5. Further, the slit lamp 1 is outfitted with a joystick 12, an eyepiece 13, an objective 14, and an adjustable head rest 15.

The halogen lamp, as part of the slit lamp 1, is in an idle state, for example, following its use. This idle state is characterized in that the regular operating voltage of the halogen lamp at the power supply 4 is reduced, for example, to 20%. In an alternative construction (not shown), the operating voltage of the halogen lamp can be completely switched off for the idle state. In the idle state, there is low energy consumption and low waste heat production by the slit lamp 1.

Concussions can be measured by the acceleration sensor 6, for example, in three dimensions. In particular, the control unit 5 can detect concussions transmitted from the floor 7 via the table 2 to the slit lamp 1 as vibrations by means of the acceleration sensor 6. Such vibrations occur particularly when a person P moves in the vicinity of the slit lamp 1. A doctor is depicted as person P. The control unit 5 can detect a person P moving in the environment of the slit lamp 1 in a noncontacting manner by means of the acceleration sensor 6. In the present embodiment form, the acceleration sensor 6 does not distinguish between different persons so that a patient, technician, nurse, or doctor's assistant moving in the surroundings can also be detected.

The control unit 5 acquires the signals of the acceleration sensor 6 in a sliding time window having, for example, a duration of two seconds. In so doing, it evaluates the amount of the vector sum of all three dimensions of the acceleration sensor 6. Values below a predeterminable minimum are ignored in the evaluation. Accordingly, a background signal noise will not lead to a false-positive person detection. The vibration amplitudes decrease as the distance from the source, i.e., from the moving person P, increases. Due to this decrease, moreover, the minimum value results in a maximum distance around the slit lamp 1 that is to be taken into account in the detection. The sensitivity of the acceleration sensor 6 and the concussions of different intensity of different persons are to be taken into account in a corresponding manner when specifying the minimum value.

When the control unit 5 determines an increase in concussion intensity within the time window, this indicates that the detected person P approaches the slit lamp 1. When the determined increase is above a predeterminable minimum increase, the control unit 5 increases the adjustable power supply 5 gradually to the normal operating voltage of the halogen lamp. The halogen lamp then reaches its operating state within a short period of time, generally before the person P arrives at the slit lamp 1. The work sequence of person P is not taken into account thereby. Due to the gradual switching to the operating state, the lifetime of the halogen lamp is hardly impaired even with frequent switching between the idle state and the operating state.

After using the slit lamp 1, i.e., after a treatment or examination of a patient (not shown), all persons P move away from the slit lamp 1 without further operating actions. Thereupon, the control unit 5 detects a time period of ten minutes of non-use and the absence of persons P, and it emits an advance warning acoustically in the form of a discrete gong sound after nine minutes. When the time period lapses, the control unit 5 readjusts the supplied voltage of the power supply 4 to 20% of the regular value in order to switch the halogen lamp to the idle state. In the alternative construction mentioned above, the operating voltage would be completely switched off to achieve minimum energy consumption.

Alternatively or in addition to the contactless detection by means of the acceleration sensor 6, other person detectors, for example, a motion detector, can be provided. For example, the joystick 12 and/or the adjusting elements (not shown) of the head rest 15 can be provided with metal contacts at their surfaces so that a detection of a present person can be derived from a touch by the operating personnel.

Figure 2:
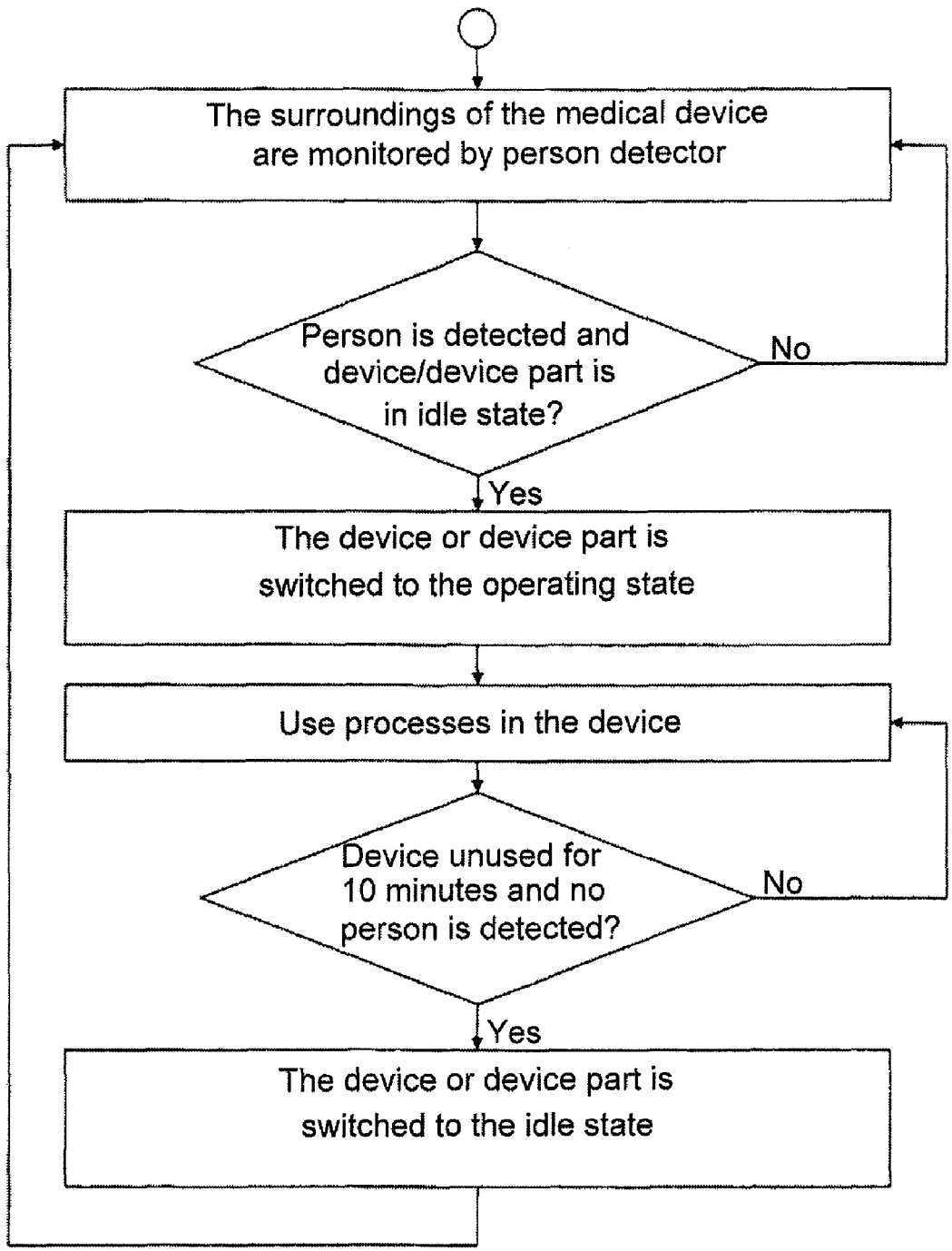
FIG. 2 a flow chart showing the control process.

FIG. 2 is a flow chart showing the flow of the control process which is carried out by the control unit 5. Of course, other durations can be predetermined for the non-use period. The duration, as well as the sensitivity of the person detector, can preferably be set at the medical device 1 itself.

FIG. 3 shows another medical device 1 in the form of an ophthalmic excimer laser for refractive surgery. The device 1 is outfitted at a monitor 8 of the laser unit/operating unit 9 with a motion detector 10 having a planar acquisition angle of 360°. The motion detector 10 is connected to a control unit 5 which is connected in turn to a laser control 11 which, in particular, regulates a temperature stabilization device (not shown).

In the initial state shown by way of example, the laser unit/operating unit 9 is in an idle state with low energy consumption. An integrated computer (not shown) is in sleep mode. The laser (not shown) and its temperature stabilization arrangement are switched off via the laser control 11 and are accordingly likewise in the idle state. A housing fan (not shown) is switched off. The energy consumption, waste heat production and noise level of the device 1 are minimal.

As soon as the motion detector 10 detects a moving person P, the control unit 5 switches all of the device parts in idle state into the operating state by means of the laser control 11. This is achieved only after a startup time of about one minute. Since the person P is detected in a noncontacting manner already upon entering the architectural interior space surrounding the device 1 and generally also carries out certain preparations for a treatment with the device 1, the device 1 is ready to use even before person P wants to use it.

After the device is used, the person P and the treated patient move away from the device 1, whereupon the control unit 5 detects a time period of twenty minutes of non-use and the absence of persons P, and can emit an acoustic or optical advance warning already after nineteen minutes. The advance warning can be switched off manually or allowed by the operating personnel. Switching off can be carried out as a general preset or case by case, particularly after the advance warning has started. When the time period of non-use expires, the control unit 5 switches all of the device parts capable of entering the idle state into the idle state for minimal energy consumption.

Alternatively or in addition, a pressure contact could be provided in the examination table as person detector. The device 1 is then switched to the operating state in due to time prior to use when the patient assumes the treatment position.

In all of the embodiment forms, the control unit 5 can be outfitted with, or programmed by, a self-learning time control which acquires and stores the use habits of the operating personnel and derives therefrom a future switching behavior for switching from the idle state to the operating state. For example, it can be derived from a few instances of use that the device 1 is used only in the presence of at least two persons. The control unit 5 will then switch the device 1 or the idling partial devices to the operating state only when two persons have been detected. A switching behavior of this kind can also be integrated into the control unit 5 directly without a self-learning time control.

In more advanced constructions, the introduction of the idle state of one or more device parts or the detection data leading to the idle state can also be outputted to external devices. In this way, for example, a printer, power outlets, a fixating light or an instrument panel externally connected to the device 1 can be switched into or out of the idle state.

In all of the embodiment forms of the invention, a monitoring of access authorization of the operating personnel can be carried out and access to the medical device 1 and the data stored therein can be granted or restricted depending on access authorization information of the detected persons P. The access authorization information which can be specified for individual persons is preferably determined from portable access authorization devices, preferably by means of short-range wireless, for example, RFID. The access rights to be determined therefrom can be accorded based on a roll and/or based on ownership with respect to data, and, for example, sub-rights can differentiate between simple reading access (data capture), writing access (data entry), maintenance access, and diagnostic/treatment access. A further differentiation can be made between types of data. For example, a group ("roll"), "medical assistant personnel" or individual assistants can be granted access only to patients' address data, but not measurements or diagnoses. By access is meant not only display on the screen, but also outputting to printers, data storage media, or data transfer over a computer network, for example, via the intranet of a medical practice or hospital, to a central computer or to another person such as the treating (in-house) physician or an outside specialist, for example, via e-mail. The access rights for these different output channels can advisably be issued in a differentiated manner so that, for example, e-mail can be sent only to selected individuals.

In addition to determining the access authorization information by means of short-range wireless, an individual password can be requested at the device 1. If the access authorization information contains a personal identification quantity, the identity of the detected person P is known. In case of unidentifiable persons P, a username can be asked for instead. Both successful and unsuccessful password inputs are advisably recorded. When a predeterminable quantity of unsuccessful attempts is exceeded, the device 1 can emit an alarm and transmit it particularly to a central monitoring unit. It is also conceivable that the device 1 changes to a locked state when a predeterminable quantity of unsuccessful attempts is exceeded such that it can only be restored to a functioning state through the intervention of service personnel. The control unit 5 preferably offers an emergency mode in which data and functions of the device 1 can be accessed even without entering a password and in spite of a possible block The use of this emergency mode should be recorded for monitoring purposes.

When the control unit 5 determines a period of non-use, particularly in connection with an absence of persons P, it can require that a password be entered again for security reasons before the device 1 can be used again. In addition, the control unit 5 can be set up for remote maintenance which is preferably possible exclusively by password interrogation and/or encryption. Any remote maintenance and all actions taken during remote maintenance should be logged along with the clock time and user identification.

The granting of access rights to individual persons P or user rolls can be carried out either on-site on the device 1 or in a central monitoring unit. In the latter case, the access rights for a plurality of medical devices 1 or all medical devices 1 (and also other devices), for example, in a doctor's office, a department of a hospital, or for an entire hospital are managed in a centralized manner. Therefore, they cannot be tampered with on premises at the device 1. Aside from restriction and/or granting of access, it is also possible to log reading access, changes to existing data, or input of new data with clock time and user identification of the operating person P. All off-premise queries or data access of the control unit 5, particularly in a central monitoring unit, should be encrypted in order to prevent tampering.

Regardless of a differentiated restriction and/or granting of access to the device 1 and its data, the access authorization information determined by short-range wireless can also optionally be used for conditional switching of one or more device parts to the operating state. The switching can be carried out in a plurality of stages, for example, depending on the access rights of the detected person P and/or depending on a distance of the person P from the device 1. The distance of the person P can be determined, for example, based on the strength of the received short-range wireless signal.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

REFERENCE NUMBERS 1 medical device
2 table
3 illumination unit
4 power supply
5 control unit
6 acceleration sensor
7 floor
8 monitor
9 laser unit/operating unit
10 motion detector
11 laser control
12 joystick
13 eyepiece
14 objective
15 head rest
P person

The invention claimed is:

1. A medical device comprising:
a device part configured to be switched between an idle state and an operating state;
a person detector configured for detecting a person; and
a control unit configured to control switching of the device part to the operating state when the person detector detects a presence of the person at a distance from the medical device;
wherein the person detector is constructed as a motion detector; and
wherein the device is an ophthalmic device.

2. The medical device according to claim 1;
wherein the person detector is configured to detect a person who is at a greater distance from the device than a distance required for using the device.

3. The medical device according to claim 1;
wherein the control unit is configured to determine whether the detected person is approaching the device and only switches to the operating state when an approach is determined.

4. The medical device according to claim 1;
wherein the device part is switched between the idle state and the operating state by a touch-sensitive operating control; and
wherein the control unit switches the device part to the operating state when the person detector detects that a person touches the operating control.

5. The medical device according to claim 1;
wherein the control unit switches the device part from the operating state to the idle state after expiration of a predeterminable or predetermined time period in which the control unit determines that the Medical device has not been used or in which the person detector does not detect any persons.

6. The medical device according to claim 5;
wherein the control unit emits a warning signal at a predeterminable or predetermined advance warning time before the expiration of the time period.

7. The medical device according to claim 1;
wherein a person in an architectural interior surrounding the device, in a room area in the surroundings of the device, or at a determined location can be detected by the person detector.

8. The medical device according to claim 1;
wherein the person detector is constructed as an acceleration sensor.

9. The medical device according to claim 1;
wherein the device is a slit lamp, a fundus camera, a device for measuring internal dimensions of the eye, or a laser.

10. The medical device according to claim 9;
wherein the partial device is a light source or a temperature stabilization device.

11. The medical device according to claim 1;
wherein a reduced operating voltage other than zero is applied to the device part in the idle state.

12. The medical device according to claim 1;
wherein the device part is configured to be electrically operated and configured to be switched between an idle state and an operating state by a control unit which switches the device part from the operating state to the idle state after expiration of a predeterminable or predetermined time period in which the control unit determines that the device has not been used.

13. The medical device according to claim 1, further comprising:
an operating control for manually switching the device from the operating state to the idle state.

14. A control method for controlling a medical device comprising at least one device part configured to be switched between an idle state and an operating state, the method comprising the steps of:
determining that the medical device has not used for a predeterminable or predetermined time period; and
switching the device part from the operating state to the idle state after the expiration of the predeterminable or predetermined time period; and
detecting a person present a distance from the medical device by means of a person detector;
wherein the device part is switched to the operating state according to the detecting step;
wherein the device is an ophthalmic device; and
wherein the person detector is constructed as at least one of a motion detector and an acceleration sensor.

15. The control method according to claim 14;
wherein the device part is switched from the operating state to the idle state after the expiration of a predeterminable or predetermined time period in which it is determined that the device has not been used or in which the person detector does not detect any persons.

16. The control method according to claim 14;
wherein a warning signal is emitted at a predeterminable or predetermined advance warning time before the time period lapses.

17. A medical device comprising:
a device part configured to be switched between an idle state and an operating state;
a person detector configured for detecting a person; and
a control unit configured to control switching of the device part to the operating state when the person detector detects a presence of the person at a distance from the medical device;
wherein the person detector is constructed as an acceleration sensor; and
wherein the device is an ophthalmic device.

* * * * *